(12) United States Patent
Ikemoto

(10) Patent No.: US 6,387,664 B1
(45) Date of Patent: May 14, 2002

(54) SPARC FUSION PROTEIN AND METHOD FOR PRODUCING THE SAME

(75) Inventor: Mitsushi Ikemoto, Ibaraki (JP)

(73) Assignee: Secretary of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/513,442

(22) Filed: Feb. 25, 2000

(30) Foreign Application Priority Data

Feb. 26, 1999 (JP) ............................................. 11-049708
Feb. 26, 1999 (JP) ............................................. 11-049826

(51) Int. Cl.$^7$ .......................... C07K 2/00; C07K 21/04; C12N 1/20; C12N 5/00; C12N 15/00

(52) U.S. Cl. .................. 435/69.7; 435/70.1; 435/252.3; 435/320.1; 435/325; 435/69.1; 530/300; 530/350; 536/23.1; 536/23.4

(58) Field of Search ........................... 424/184.1, 185.1, 424/192.1; 435/41, 69.1, 69.7, 70.1, 320.1, 325, 252.3; 514/2; 530/300, 350, 412; 536/23.1, 23.5, 23.4

(56) References Cited

U.S. PATENT DOCUMENTS

| | | | | | |
|---|---|---|---|---|---|
| 5,270,181 | A | * | 12/1993 | McCoy et al. .............. | 435/69.7 |
| 5,646,016 | A | * | 7/1997 | McCoy et al. .............. | 435/69.7 |
| 5,858,724 | A | * | 1/1999 | Novy, Jr. et al. .......... | 435/69.6 |

FOREIGN PATENT DOCUMENTS

| | | | |
|---|---|---|---|
| WO | WO 98/20112 | * | 5/1998 |

OTHER PUBLICATIONS

Engel et el. Calcium binding domains and calcium–induced conformational transition of SPARC/BM–40/Osteonectin, and extracellular glycoprotein expressed in mineralized and nonmineralized tissues. Biochemistry 26: 6958–6965, 1987.*
Howe, et al. Expression of SPARC/osteonectin transcript in murine embryos and gonads. Differentiation 37: 20–25, 1988.*
Lankat–Buttgereit et al. Cloning and complete amino acid sequences of human and murine basement membrane protein BM–40 (SPARC, osteonectin), FEBS Letters 236(2): 352–356, 1988.*
LaVallie et al. Thioredoxin gene fusion expression system that circumvents inclusion body formation in the E. coli cytoplasm. Bio/Technology 11: 187–193, 1993.*
Mason et al. Evidence from molecular cloning that SPARC, a major product of mouse embryo parietal endoderm, is related to an endothelial cell "culture shock" glycoprotein of M 43, 000. Embo J 5(7) 1465–1472. 1986.
Mayer et al. Calcium–dependent binding of basement protein BM–40 (osteonectin, SPARC) to basement membrane collagen type IV. Eur J Biochem 198: 141–150, 1991.

Mendis et al. Developmental expression in the rat cerebellum of SC1, a putative brain extracellular matrix glycoprotein related to SPARC. Brain Research 633: 197–205, 1994.
Mendis et al. SC1, a brain extracellular matrix glycoprotein related to SPARC and follistain, is expressed by rat cerebellar astrocytes following injury and during development. Brain Research 730: 95–106, 1996.
Porter et al. Distribution of SPARC in normal and neoplastic tissue. J Histochem and Cytochem 43(8): 791–800, 1995.*
Rempel et al. SPARC: a potential diagnostic marker of invasive meningiomas. Clin Cancer Res 5: 237–241, 1999.*
Schneider et al. Manipulating the aggregation and oxidation of SPARC in the cytoplasm of *Escherichia coli*. Nature Biotechnology 15(6): 581–585, 1997.*
Soderling et al. Cloning and expression of murine SC1, a gene product homologous to SPARC. J Histochem and Cytochem 45(6): 823–835, 1997.*
Swaroop et al. Molecular analysis of the cDNA for human SPARC/osteonectin/BM–40: sequence, expression, and localization of the gene to chromosome 5q31–q33. Genomics 2: 37–47, 1988.*
Ikemoto et al. Increased sensitivity to the stimulant effects of morphine conferred by anti–adhesive glycoprotein SPARC in amygdala. Nature Medicine 6(8): 910–915, 2000.*
Skolnick et al. From genes to protein structure and function. novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics (5(4): 132–133, 1999.*
Bork et al. Go hunting in sequence databases but watch out for the traps. Trends in Genetics. 12(10): 425–427, 1996.*
Wells. J.A. Additivity of mutational effects in protein. Biochemistry 29 (37): 8509–8517, 1990.*

(List continued on next page.)

*Primary Examiner*—Elizabeth Kemmerer
*Assistant Examiner*—Bridget E. Bunner
(74) *Attorney, Agent, or Firm*—Medlen & Carroll, LLP

(57) ABSTRACT

The present invention provides a secreted protein acidic and rich in cysteine (SPARC) fusion protein obtainable by fusing SPARC to thioredoxin; a nucleic acid encoding the fusion protein; a recombinant vector capable of expressing the fusion protein, a method for producing and purifying the fusion protein; and a research reagent or pharmaceutical composition comprising the fusion protein as an active ingredient. In particular, the present invention relates to the use of a thioredoxin SPARC fusion protein for basic research in neurobiology and/or to its use for treating various neuropathologies.

9 Claims, 9 Drawing Sheets

OTHER PUBLICATIONS

Ngo et al. Computational complexity, protein structure prediction, and the Levinthal paradox. The Protein Folding Problem and Tertiary Structure Prediction, pp. 492–495, 1994.*

Chomczynski et al., "Single–Step Method of RNA Isolation by Acid Guaninidium Thiocyanate–Phenol–Chloroform Extraction," Anal. Biochem. 162: 156–159 (1987).

Lane et al., "The biology of SPARC, a protein that modulates cell–matrix interactions," FASEB J. 8: 163–173 (1994).

Mann et al., "Solubilization of protein BM–40 from a basement membrane tumor with chelating agents and evidence for its identify with osteonectin and SPARC," FEBS Lett. 218: 167–172 (1987).

Marchuk et al., "Construction of T–vectors, a rapid and general system for direct cloning of unmodified PCR products," Nucl. Acids Res. 19: 1154 (1991).

McVey et al., "Characterization of the Mouse SPARC/Osteonectin Gene Intron/Exon Organization and An Unusual Promoter Region," J. Biol. Chem. 263: 11111–11116 (1988);.

Murphy–Ullrich et al., "SPARC Mediates Focal Adhesion Disassembly in Endothelial Cells Through a Follistatin –Like Region and the $Ca^{2+}$–Binding EF–Hand," J. Cell. Biology 57: 341–350 (1995).

Okayama et al., "High–Efficiency Cloning of Full–Length cDNA: Construction and Screening of cDNA Expression Libraries for Mammalian Cells," Meth. Enzymol. 154: 3–28 (1987).

Sage et al., "Characterization of a Novel Serum Albumin –binding Glycoprotein Secreted by Endothelial Cells in Culture," J. Biol. Chem. 259: 3993–4007 (1984).

Sage et al., "Extracellular Proteins That Modulate Cell–Matrix Interactions. SPARC, Tenascin, and Thrombospondin," J. Biol. Chem. 266: 14831–14834 (1991).

Sambrook et al., in *Molecular Cloning: A Laboratory Manual, Second Edition*, Cold Spring Harbor Laboratory Press (1989).

Thermine et al., "Osteonectin, A Bone–Specific Protein Linking Mineral to Collagen," Cell 26: 99–105 (1981).

* cited by examiner

FIG. 1

MSDKIIHLTDDSFDTDVLKADGAILVDFWAEWCGPCKMIAPILDEIADEYQGKLTVAKLN

IDQNPGTAPKYGIRGIPTLLLFKNGEVAATKVGALSKGQLKEFLDANLAGSGSGHMHHHH

HHSSGLVPRGSGMKETAAAKFERQHMDSPDLGTDDDDKAMADIGS MRAWIFFLLCLAGRA

LAAPQQTEVAEEIVEEETVVEETGVPVGANPVQVEMGEFEDGAEETVEEVVADNPCQNHH

CKHGKVCELDESNTPMCVCQDPTSCPAPIGEFEKVCSNDNKTFDSSCHFFATKCTLEGTK

KGHKLHLDYIGPCKYIAPCLDSELTEFPLRMRDWLKNVLVTLYERDEGNNLLTEKQKLRV

KKIHENEKRLEAGDHPVELLARDFEKNYNMYIFPVHWQFGQLDQHPIDGYLSHTELAPLR

APLIPMEHCTTRFFETCDLDNDKYIALEEWAGCFGIKEQDINKDLVI//

Underlined portion: amino acid sequence representing thioredoxin form pET32a(+) vector Other portion: amino acid sequence representing full-length SPARC Lane 1: SPARC fusion protein Lane 2: Thioredoxin M: Molecular weight marker

SEQUENCE LISTING

<160> NUMBER OF SEQ ID NOS: 4

<210> SEQ ID NO 1
<211> LENGTH: 7375
<212> TYPE: DNA
<213> ORGANISM: Mus musculus
<220> FEATURE:
<221> NAME/KEY: CDS
<222> LOCATION: (5209)..(6609)

<400> SEQUENCE: 1

```
tggcgaatgg gacgcgccct gtagcggcgc attaagcgcg gcgggtgtgg tggttacgcg      60
cagcgtgacc gctacacttg ccagcgccct agcgcccgct cctttcgctt tcttcccttc     120
ctttctcgcc acgttcgccg gctttccccg tcaagctcta aatcgggggc tccctttagg     180
gttccgattt agtgctttac ggcacctcga ccccaaaaaa cttgattagg gtgatggttc     240
acgtagtggg ccatcgccct gatagacggt ttttcgccct ttgacgttgg agtccacgtt     300
ctttaatagt ggactcttgt tccaaactgg aacaacactc aaccctatct cggtctattc     360
ttttgattta taagggattt tgccgatttc ggcctattgg ttaaaaaatg agctgattta     420
acaaaaattt aacgcgaatt ttaacaaaat attaacgttt acaatttcag gtggcacttt     480
tcggggaaat gtgcgcggaa cccctatttg tttattttc taaatacatt caaatatgta     540
tccgctcatg agacaataac cctgataaat gcttcaataa tattgaaaaa ggaagagtat     600
gagtattcaa catttccgtg tcgcccttat ccctttttt gcggcatttt gccttcctgt     660
ttttgctcac ccagaaacgc tggtgaaagt aaaagatgct gaagatcagt tgggtgcacg     720
agtgggttac atcgaactgg atctcaacag cggtaagatc cttgagagtt tcgccccga     780 agaacgtttt ccaatgatga gcacttttaa agttctgcta tgtggcgcgg tattatcccg     840
tattgacgcc gggcaagagc aactcggtcg ccgcatacac tattctcaga atgacttggt     900
tgagtactca ccagtcacag aaaagcatct tacggatggc atgacagtaa gagaattatg     960
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200 ccgcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
```

-continued

```
aggatcttct tgagatcctt tttttctgcg cgtaatctgc tgcttgcaaa caaaaaaacc      1680
accgctacca gcggtggttt gtttgccgga tcaagagcta ccaactcttt ttccgaaggt      1740
aactggcttc agcagagcgc agataccaaa tactgtcctt ctagtgtagc cgtagttagg      1800
ccaccacttc aagaactctg tagcaccgcc tacatacctc gctctgctaa tcctgttacc      1860
agtggctgct gccagtggcg ataagtcgtg tcttaccggg ttggactcaa gacgatagtt      1920
accggataag gcgcagcggt cgggctgaac ggggggttcg tgcacacagc ccagcttgga      1980
gcgaacgacc tacaccgaac tgagatacct acagcgtgag ctatgagaaa gcgccacgct      2040
tcccgaaggg agaaaggcgg acaggtatcc ggtaagcggc agggtcggaa caggagagcg      2100
cacgagggag cttccagggg gaaacgcctg gtatctttat agtcctgtcg ggtttcgcca      2160
cctctgactt gagcgtcgat ttttgtgatg ctcgtcaggg gggcggagcc tatggaaaaa      2220
cgccagcaac gcggcctttt tacggttcct ggccttttgc tggccttttg ctcacatgtt      2280
ctttcctgcg ttatcccctg attctgtgga taaccgtatt accgcctttg agtgagctga      2340
taccgctcgc cgcagccgaa cgaccgagcg cagcgagtca gtgagcgagg aagcggaaga      2400
gcgcctgatg cggtattttc tccttacgca tctgtgcggt atttcacacc gcatatatgg      2460
tgcactctca gtacaatctg ctctgatgcc gcatagttaa gccagtatac actccgctat      2520
cgctacgtga ctgggtcatg gctgcgcccc gacacccgcc aacacccgct gacgcgccct      2580
gacgggcttg tctgctcccg gcatccgctt acagacaagc tgtgaccgtc tccgggagct      2640
gcatgtgtca gaggttttca ccgtcatcac cgaaacgcgc gaggcagctg cggtaaagct      2700
catcagcgtg gtcgtgaagc gattcacaga tgtctgcctg ttcatccgcg tccagctcgt      2760
tgagtttctc cagaagcgtt aatgtctggc ttctgataaa gcgggccatg ttaagggcgg      2820
ttttttcctg tttggtcact gatgcctccg tgtaaggggg atttctgttc atgggggtaa      2880
tgataccgat gaaacgagag aggatgctca cgatacgggt tactgatgat gaacatgccc      2940
ggttactgga acgttgtgag ggtaaacaac tggcggtatg gatgcggcgg gaccagagaa      3000
aaatcactca gggtcaatgc cagcgcttcg ttaatacaga tgtaggtgtt ccacagggta      3060
gccagcagca tcctgcgatg cagatccgga acataatggt gcagggcgct gacttccgcg      3120
tttccagact ttacgaaaca cggaaaccga agaccattca tgttgttgct caggtcgcag      3180
acgttttgca gcagcagtcg cttcacgttc gctcgcgtat cggtgattca ttctgctaac      3240
cagtaaggca acccegecag cctagccggg tcctcaacga caggagcacg atcatgcgca      3300
cccgtggggc cgccatgccg gcgataatgg cctgcttctc gccgaaacgt ttggtggcgg      3360
gaccagtgac gaaggcttga gcgagggcgt gcaagattcc gaataccgca agcgacaggc      3420
cgatcatcgt cgcgctccag cgaaagcggt cctcgccgaa aatgacccag agcgctgccg      3480
gcacctgtcc tacgagttgc atgataaaga agacagtcat aagtgcggcg acgatagtca      3540
tgccccgcgc ccaccggaag gagctgactg ggttgaaggc tctcaagggc atcggtcgag      3600
atcccggtgc ctaatgagtg agctaactta cattaattgc gttgcgctca ctgcccgctt      3660
tccagtcggg aaacctgtcg tgccagctgc attaatgaat cggccaacgc gcgggagag      3720 gcggtttgcg tattgggcgc cagggtggtt tttcttttca ccagtgagac gggcaacagc      3780
tgattgccct tcaccgcctg gccctgagag agttgcagca agcggtccac gctggtttgc      3840
cccagcaggc gaaaatcctg tttgatggtg gttaacggcg ggatataaca tgagctgtct      3900
tcggtatcgt cgtatcccac taccgagatg tccgcaccaa cgcgcagccc ggactcgta       3960 atggcgcgca ttgcgcccag cgccatctga tcgttggcaa ccagcatcgc agtgggaacg      4020
```

-continued

```
atgccctcat tcagcatttg catggtttgt tgaaaaccgg acatggcact ccagtcgcct     4080
tcccgttccg ctatcggctg aatttgattg cgagtgagat atttatgcca gccagccaga     4140
cgcagacgcg ccgagacaga acttaatggg cccgctaaca gcgcgatttg ctggtgaccc     4200
aatgcgacca gatgctccac gcccagtcgc gtaccgtctt catgggagaa aataatactg     4260
ttgatgggtg tctggtcaga gacatcaaga aataacgccg gaacattagt gcaggcagct     4320
tccacagcaa tggcatcctg gtcatccagc ggatagttaa tgatcagccc actgacgcgt     4380
tgcgcgagaa gattgtgcac cgccgcttta caggcttcga cgccgcttcg ttctaccatc     4440
gacaccacca cgctggcacc cagttgatcg gcgcgagatt taatcgccgc gacaatttgc     4500
gacggcgcgt gcagggccag actggaggtg caacgccaa tcagcaacga ctgtttgccc      4560
gccagttgtt gtgccacgcg gttgggaatg taattcagct ccgccatcgc cgcttccact     4620
ttttcccgcg ttttcgcaga aacgtggctg gcctggttca ccacgcggga aacggtctga     4680
taagagacac cggcatactc tgcgacatcg tataacgtta ctggtttcac attcaccacc     4740
ctgaattgac tctcttccgg gcgctatcat gccataccgc gaaaggtttt gcgccattcg     4800
atggtgtccg ggatctcgac gctctccctt atgcgactcc tgcattagga agcagcccag     4860
tagtaggttg aggccgttga gcaccgccgc cgcaaggaat ggtgcatgca aggagatggc     4920
gcccaacagt cccccggcca cggggcctgc caccataccc acgccgaaac aagcgctcat     4980
gagcccgaag tggcgagccc gatcttcccc atcggtgatg tcggcgatat aggcgccagc     5040
aaccgcacct gtggcgccgg tgatgccggc cacgatgcgt ccggcgtaga ggatcgagat     5100
cgatctcgat cccgcgaaat taatacgact cactataggg gaattgtgag cggataacaa     5160
ttcccctcta gaaataattt tgtttaactt taagaaggag atatacat atg agc gat      5217
                                                      Met Ser Asp
                                                        1 aaa att att cac ctg act gac gac agt ttt gac acg gat gta ctc aaa       5265
Lys Ile Ile His Leu Thr Asp Asp Ser Phe Asp Thr Asp Val Leu Lys
    5              10                  15 gcg gac ggg gcg atc ctc gtc gat ttc tgg gca gag tgg tgc ggt ccg       5313
Ala Asp Gly Ala Ile Leu Val Asp Phe Trp Ala Glu Trp Cys Gly Pro
 20             25                   30                  35 tgc aaa atg atc gcc ccg att ctg gat gaa atc gct gac gaa tat cag       5361
Cys Lys Met Ile Ala Pro Ile Leu Asp Glu Ile Ala Asp Glu Tyr Gln
             40                  45                  50 ggc aaa ctg acc gtt gca aaa ctg aac atc gat caa aac cct ggc act       5409
Gly Lys Leu Thr Val Ala Lys Leu Asn Ile Asp Gln Asn Pro Gly Thr
         55                  60                  65 gcg ccg aaa tat ggc atc cgt ggt atc ccg act ctg ctg ctg ttc aaa       5457
Ala Pro Lys Tyr Gly Ile Arg Gly Ile Pro Thr Leu Leu Leu Phe Lys
     70                  75                  80 aac ggt gaa gtg gcg gca acc aaa gtg ggt gca ctg tct aaa ggt cag       5505
Asn Gly Glu Val Ala Ala Thr Lys Val Gly Ala Leu Ser Lys Gly Gln
 85                  90                  95 ttg aaa gag ttc ctc gac gct aac ctg gcc ggt tct ggt tct ggc cat       5553
Leu Lys Glu Phe Leu Asp Ala Asn Leu Ala Gly Ser Gly Ser Gly His
100                 105                 110                 115 atg cac cat cat cat cat cat tct tct ggt ctg gtg cca cgc ggt tct       5601
Met His His His His His His Ser Ser Gly Leu Val Pro Arg Gly Ser
                120                 125                 130 ggt atg aaa gaa acc gct gct gct aaa ttc gaa cgc cag cac atg gac       5649
Gly Met Lys Glu Thr Ala Ala Ala Lys Phe Glu Arg Gln His Met Asp
        135                 140                 145
```

```
agc cca gat ctg ggt acc gac gac gac gac aag gcc atg gct gat atc     5697
Ser Pro Asp Leu Gly Thr Asp Asp Asp Asp Lys Ala Met Ala Asp Ile
        150                 155                 160 gga tcc atg agg gcc tgg atc ttc ttt ctc ctt tgc ctg gcc ggg agg     5745
Gly Ser Met Arg Ala Trp Ile Phe Phe Leu Leu Cys Leu Ala Gly Arg
    165                 170                 175 gcc ctg gca gcc cct cag cag act gaa gtt gct gag gag ata gtg gag     5793
Ala Leu Ala Ala Pro Gln Gln Thr Glu Val Ala Glu Glu Ile Val Glu
180                 185                 190                 195 gag gaa acc gtg gtg gag gag aca ggg gta cct gtg ggt gcc aac cca     5841
Glu Glu Thr Val Val Glu Glu Thr Gly Val Pro Val Gly Ala Asn Pro
                200                 205                 210 gtc cag gtg gaa atg gga gaa ttt gag gac ggt gca gag gaa acg gtc     5889
Val Gln Val Glu Met Gly Glu Phe Glu Asp Gly Ala Glu Glu Thr Val
            215                 220                 225 gag gag gtg gtg gct gac aac ccc tgc cag aac cat cat tgc aaa cat     5937
Glu Glu Val Val Ala Asp Asn Pro Cys Gln Asn His His Cys Lys His
        230                 235                 240 ggc aag gtg tgt gag ctg gac gag agc aac acc ccc atg tgt gtg tgc     5985
Gly Lys Val Cys Glu Leu Asp Glu Ser Asn Thr Pro Met Cys Val Cys
    245                 250                 255 cag gac ccc acc agc tgc cct gct ccc att ggc gag ttt gag aag gta     6033
Gln Asp Pro Thr Ser Cys Pro Ala Pro Ile Gly Glu Phe Glu Lys Val
260                 265                 270                 275 tgc agc aat gac aac aag acc ttc gac tct tcc tgc cac ttc ttt gcc     6081
Cys Ser Asn Asp Asn Lys Thr Phe Asp Ser Ser Cys His Phe Phe Ala
                280                 285                 290 acc aag tgc acc ctg gag ggc acc aag aag ggc cac aag ctc cac ctg     6129
Thr Lys Cys Thr Leu Glu Gly Thr Lys Lys Gly His Lys Leu His Leu
            295                 300                 305 gac tac atc gga cca tgc aaa tac atc gcc ccc tgc ctg gat tcc gag     6177
Asp Tyr Ile Gly Pro Cys Lys Tyr Ile Ala Pro Cys Leu Asp Ser Glu
        310                 315                 320 ctg acc gaa ttc cct ctg cgc atg cgt gac tgg ctc aaa aat gtc ctg     6225
Leu Thr Glu Phe Pro Leu Arg Met Arg Asp Trp Leu Lys Asn Val Leu
    325                 330                 335 gtc acc ttg tac gag aga gat gag ggc aac aac ctc ctc act gag aag     6273
Val Thr Leu Tyr Glu Arg Asp Glu Gly Asn Asn Leu Leu Thr Glu Lys
340                 345                 350                 355 cag aag ctg cgt gtg aag aag atc cat gag aac gag aag cgc ctg gag     6321
Gln Lys Leu Arg Val Lys Lys Ile His Glu Asn Glu Lys Arg Leu Glu
                360                 365                 370 gct gga gac cac ccc gtg gag ctg ttg gcc cga gac ttt gag aag aac     6369
Ala Gly Asp His Pro Val Glu Leu Leu Ala Arg Asp Phe Glu Lys Asn
            375                 380                 385 tac aat atg tac atc ttc cct gtc cac tgg cag ttt ggc cag ctg gat     6417
Tyr Asn Met Tyr Ile Phe Pro Val His Trp Gln Phe Gly Gln Leu Asp
        390                 395                 400 cag cac cct att gat ggg tac ctg tcc cac act gag ctg gcc cca ctg     6465
Gln His Pro Ile Asp Gly Tyr Leu Ser His Thr Glu Leu Ala Pro Leu
    405                 410                 415 cgt gct ccc ctc atc ccc atg gaa cat tgc acc aca cgt ttc ttt gag     6513
Arg Ala Pro Leu Ile Pro Met Glu His Cys Thr Thr Arg Phe Phe Glu
420                 425                 430                 435 acc tgt gac cta gac aac gac aag tac att gcc ctg gag gaa tgg gcc     6561
Thr Cys Asp Leu Asp Asn Asp Lys Tyr Ile Ala Leu Glu Glu Trp Ala
                440                 445                 450 ggc tgc ttt ggc atc aag gag cag gac atc aac aag gat ctg gtg atc     6609
Gly Cys Phe Gly Ile Lys Glu Gln Asp Ile Asn Lys Asp Leu Val Ile
            455                 460                 465
```

```
taagttcacg cctcctgctg cagtcctgaa ctctctccct ctgatgtgtc cccctccca      6669 ttacccccctt gtttaaaatg tttggatggt tggctgttcc gcctggggat aaggtgctaa    6729
catagattta actgaataca ttaacggtgc taaaaaaaaa aaaaaaacaa ggtaagaaag     6789
aaactagaac ccaagtctca gcattttccc acataactct gaggccatgg cccatccaca    6849
gcctcctggt ccctgcact  acccagtgtc tcactggctg tgttggaaac ggacttgtat    6909
aagctcaccg ccacaagca cgagatatct ctagctttca tttctgtttt gcatttgact    6969
cttaacactc acccagactc tgtgcttatt tcattttggg ggatgtgggc ttttccct     7029 ggtggtttgg agttaggcag agggaagtta cagacacagg tacaaaattt gggtaaagat    7089
actgtgagac ctgaggaccc accagtcaga acccacatgg caagtcttag tagcctaggt    7149
caaggaaaga cagaataatc cagagctgtg gcacacatga cagactccca gcagcccggt    7209
cgactcgagc accaccacca ccaccactga gatccggctg ctaacaaagc ccgaaggaa     7269 gctgagttgg ctgctgccac cgctgagcaa taactagcat aaccccttgg ggcctctaaa    7329
cgggtcttga ggggttttttt gctgaaagga ggaactatat ccggat                  7375
```

<210> SEQ ID NO 2
<211> LENGTH: 467
<212> TYPE: PRT
<213> ORGANISM: Mus musculus

<400> SEQUENCE: 2

```
Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
                 20                  25                  30

Cys Gly Pro Cys Lys Met Ile Ala Pro Ile Leu Asp Glu Ile Ala Asp
             35                  40                  45

Glu Tyr Gln Gly Lys Leu Thr Val Ala Lys Leu Asn Ile Asp Gln Asn
         50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met
145                 150                 155                 160

Ala Asp Ile Gly Ser Met Arg Ala Trp Ile Phe Phe Leu Leu Cys Leu
                165                 170                 175

Ala Gly Arg Ala Leu Ala Ala Pro Gln Gln Thr Glu Val Ala Glu Glu
            180                 185                 190
```

```
Ile Val Glu Glu Thr Val Val Glu Thr Gly Val Pro Val Gly
        195                 200                 205

Ala Asn Pro Val Gln Val Glu Met Gly Glu Phe Glu Asp Gly Ala Glu
        210                 215                 220

Glu Thr Val Glu Glu Val Val Ala Asp Asn Pro Cys Gln Asn His His
225                 230                 235                 240

Cys Lys His Gly Lys Val Cys Glu Leu Asp Glu Ser Asn Thr Pro Met
                245                 250                 255

Cys Val Cys Gln Asp Pro Thr Ser Cys Pro Ala Pro Ile Gly Glu Phe
                260                 265                 270

Glu Lys Val Cys Ser Asn Asp Asn Lys Thr Phe Asp Ser Ser Cys His
            275                 280                 285

Phe Phe Ala Thr Lys Cys Thr Leu Glu Gly Thr Lys Lys Gly His Lys
        290                 295                 300

Leu His Leu Asp Tyr Ile Gly Pro Cys Lys Tyr Ile Ala Pro Cys Leu
305                 310                 315                 320

Asp Ser Glu Leu Thr Glu Phe Pro Leu Arg Met Arg Asp Trp Leu Lys
                325                 330                 335

Asn Val Leu Val Thr Leu Tyr Glu Arg Asp Glu Gly Asn Asn Leu Leu
                340                 345                 350

Thr Glu Lys Gln Lys Leu Arg Val Lys Lys Ile His Glu Asn Glu Lys
            355                 360                 365

Arg Leu Glu Ala Gly Asp His Pro Val Glu Leu Leu Ala Arg Asp Phe
370                 375                 380

Glu Lys Asn Tyr Asn Met Tyr Ile Phe Pro Val His Trp Gln Phe Gly
385                 390                 395                 400

Gln Leu Asp Gln His Pro Ile Asp Gly Tyr Leu Ser His Thr Glu Leu
                405                 410                 415

Ala Pro Leu Arg Ala Pro Leu Ile Pro Met Glu His Cys Thr Thr Arg
            420                 425                 430

Phe Phe Glu Thr Cys Asp Leu Asp Asn Asp Lys Tyr Ile Ala Leu Glu
        435                 440                 445

Glu Trp Ala Gly Cys Phe Gly Ile Lys Glu Gln Asp Ile Asn Lys Asp
    450                 455                 460

Leu Val Ile
465

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 3
ccgagagttc ccagcatcat                                          20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic

<400> SEQUENCE: 4
tcaaaccaat tcaccagtct                                          20
```

SPARC FUSION PROTEIN AND METHOD FOR PRODUCING THE SAME

FIELD OF THE INVENTION

The present invention relates to a SPARC fusion protein and a method for producing the protein. The invention also relates to a pharmaceutical composition comprising the SPARC fusion protein. More specifically, the invention relates to a pharmaceutical composition for use in inhibiting nerve cell adhesion to thereby cause nerve cell migration, or for use in promoting neurite degeneration to thereby cause neuroplasticity.

BACKGROUND OF THE INVENTION

SPARC (a secreted protein acidic and rich in cysteine) was originally reported as osteonectin which is a major noncollagenous protein present in bone (Thermine, J. D. et al., Cell, 26: 99–105, 1981), and has attracted attention as a functional bone-specific protein since it exhibits strong binding to collagen and hydroxyapatite and has Ca 2+binding activity. A gene encoding SPARC has been sequenced from a 43 kDa protein which is secreted by cells when adhesive cultured cells proliferate (Sage, H. et al., J. Biol. Chem., 259, 3993–4007, 1984). Later, it was also found that SPARC is identical to BM-40 isolated from the basement membrane by another group of researchers (Mann, K. et al., FEBS Lett., 218: 162172, 1987). Since then, secretion of SPARC has been observed in various cultured cells. In particular, secretion from normal fibroblasts and vascular endothelial cells is constitutive (Lane, T. F. & Sage, E. H., FASEB J., 8: 163–173, 1994).

As to functions of SPARC, it is known that when added to cultured cell systems, SPARC inhibits cell adhesion to extracellular matrix molecules in a concentration-dependent manner, and thus SPARC is called the "anti-adhesive protein" together with thrombospondin and tenascin (Sage, E. H. & Bornstein, P., J. Biol. Chem., 266: 14831–14834, 1991). It has been reported that this action of SPARC is not exerted by competitive inhibition of the binding between integrins and cell adhesion ligands but exerted by acting on cytoskeleton systems such as vinculin via intracellular signal transduction to thereby degrade focal adhesion plaques (Murphy-Ullrich, J. E. et al., J. Cell. Biochem., 57: 341–350, 1995). Most remarkably, SPARC reduces the production of ECM (extracellular matrix) and enhances the production of ECM-degrading proteases (Lane, T. F. & Sage, E. H., FASEB J., 8: 163–173, 1994). At the same time, SPARC is expressed highly at sites undergoing angiogenesis and reduces the secretion of fibronectin and thrombospondin in vascular endothelial cells. Thus, SPARC remodels ECM through combination of the above-described actions. In particular, it is believed that SPARC controls cell proliferation and promotes the increase of intracellular permeability in vascular endothelial cells and is essential for the expression of cell proliferating action and angiogenesis activity.

Since SPARC has various physiological activities as described above, its utility as a therapeutic is attracting attention, and clinical application of SPARC is expected.

Several attempts have been made to produce SPARC by recombinant DNA techniques using animal cells as a host cell. However, the yields were very low, and several stages of purification were needed. Thus, such methods required great labor and cost. Although there have been some attempts using Escherichia coli as a host cell, SPARC was not eluted into soluble fractions or eluted thereinto only in an extremely small amount. Besides, SPARC accumulated in inclusion bodies (which are insoluble fractions) was an inactive-type SPARC not retaining its physiological activities. A method for obtaining an active-type SPARC by appropriately folding the S—S bond in the inactive-type SPARC isolated/purified from insoluble fractions has not been established yet. Even if SPARC is expressed as a fusion protein fused to glutathione-S-transferase (GST) or the like, the protein is also accumulated in inclusion bodies. Thus, any of such methods has not achieved production of SPARC in large quantities.

The above-described functions of SPARC relating to angiogenesis have been only confirmed in vascular endothelial cells. However, no reports have been made about functions of SPARC in nerve cells.

Substances which induce long-term changes in synapse function(s), such as that brought about by the administration of psychotropics like morphine, have not yet been described. Morphine and other narcotic analgesics that have a strong affinity for the opioid $\mu$ receptor have qualitatively almost identical pharmacological effects including: analgesic, psychological (sense of intoxication), sedative, respiration-inhibitory, vomiting, and cardiovascular effects. Thus, they are used for post-operational pain, pain of end-stage cancer, pain of cardiac infarction, etc. as an analgesic or for treating dyspnea brought about by acute pulmonary edema or acute left ventricular failure. However, though morphine exhibits a remarkable effect on pain, its use for chronic diseases causes problems of tolerance and dependence. Thus, use of morphine is restricted to the specific diseases described above. Repeated administration of morphine easily leads to tolerance, as well as physical and mental dependence. The shorter the administration interval, the quicker tolerance and dependence are formed. For example, if morphine administration is suddenly suspended or naloxone (an antagonist) is administered after the formation of physical dependence, diversified withdrawal symptoms such as trembling, anxiety, insomnia, convulsion, sweating, rhinorrhea, lacrimation, fever, rise in blood pressure, tachycardia, mydriasis, diarrhea, bellyache, vomiting, etc. appear. Since the above-described tolerance and dependence are retained for months or years, it is believed that changes are occurring in the function of synapses for a long period of time.

SUMMARY OF THE INVENTION

It is an object of the invention to generate and use SPARC as a therapeutic agent because of its various physiological activities and because it can be produced efficiently, economically, and in a large quantity.

It is another object of the invention to search and elucidate those substances which are involved in every change that occurs in neurons and synapses (such as proliferation, adhesion, migration, excitement) and to provide such substances as pharmaceutical compositions which are available for studying mechanisms of the nervous system and for prophylactic treatment of nervous diseases relating thereto.

As a result of intensive and extensive researches toward the solution of the above problems, the present inventors have found that by incorporating a gene encoding SPARC downstream of a gene encoding thioredoxin and expressing the resultant construct in E. coli, it is possible to produce SPARC as an easy-to-formulate, soluble protein in a large quantity without losing the physiological activities of SPARC.

Also, the present inventors have isolated and identified a group of genes the expression of which is specifically increased in the amygdala during chronic administration of morphine, and found that one of the genes is SPARC gene. Then, based on the above facts, the inventors have prepared a SPARC fusion protein and administered it together with morphine, and confirmed that morphine-induced spontaneous locomotor activity increases in the brain as a result of the administration. This means that synapse functions are changing. The inventors have also confirmed that the SPARC fusion protein exerts anti-cell adhesion activity and cell-rounding activity on nerve cells. Thus, the present invention has been achieved.

In the first aspect, the present invention relates to the following protein (a) or (b):
(a) a protein consisting of the amino acid sequence as shown in SEQ ID NO:2 of the Sequence Listing
(b) a protein which consists of the amino acid sequence as shown in SEQ ID NO:2 of the Sequence Listing having deletion, substitution or addition of one or several amino acids and which has physiological activities of SPARC.

The deletion, substitution or addition of amino acids can be introduced by site-specific mutagenesis, a technique well known in the art before the filing of the present application. The term "one or several amino acids" means such a number of amino acids that can be deleted, substituted or added by site-specific mutagenesis.

The "physiological activities of SPARC" mentioned above refers to angiogenesis, anti-cell adhesion activity (cell elongation inhibitory activity and cell-rounding activity), extracellular matrix remodeling (reduction of extracellular matrix production and enhancement of production of extracellular matrix-degrading proteases), bone formation (mineralization) and the like.

In the second aspect, the present invention relates to a DNA coding for the above-described protein, or a DNA consisting of a partial nucleotide sequence spanning from position 5209 to position 6609 of the nucleotide sequence as shown in SEQ ID NO:1 of the Sequence Listing.

In the third aspect, the present invention relates to a method for producing a SPARC fusion protein, comprising culturing in a medium a transformant obtainable by introducing into a host cell a recombinant vector incorporating the above-described DNA, allowing the host cell to produce and accumulate the protein encoded by the DNA in the resultant culture, and recovering the protein from the culture.

In the fourth aspect, the present invention relates to a pharmaceutical composition comprising the above-described protein.

DESCRIPTION OF THE DRAWINGS

FIG. 1 shows the entire amino acid sequence of the SPARC fusion protein of the invention (SEQ ID NO:2). Abbreviations used in this FIG. are as follows:
  A: alanine (Ala)
  R: arginine (Arg)
  N: asparagine (Asn)
  D: aspartic acid (Asp)
  C: cysteine (Cys)
  Q: glutamine (Gln)
  E: glutamic acid (Glu)
  G: glycine (Gly)
  H: histidine (His)
  I: isoleucine (Ile)
  L: leucine (Leu)
  K: lysine (Lys)
  M: methionine (Met)
  F: phenylalanine (Phe)
  P: proline (Pro)
  S: serine (Ser)
  T: threonine (Thr)
  W: tryptophan (Trp)
  Y: tyrosine (Tyr)
  V: valine (Val)

FIG. 4, Panel B shows amount ratios of SPARC MRNA expression at the basolateral amnygdala nucleus (BL) of the amygdala and at the locus ceruleus (LC) outside of the amygdala in administration group mice to that expression at corresponding sites in control mice (physiological saline alone).

DESCRIPTION OF THE INVENTION

Figure 2:
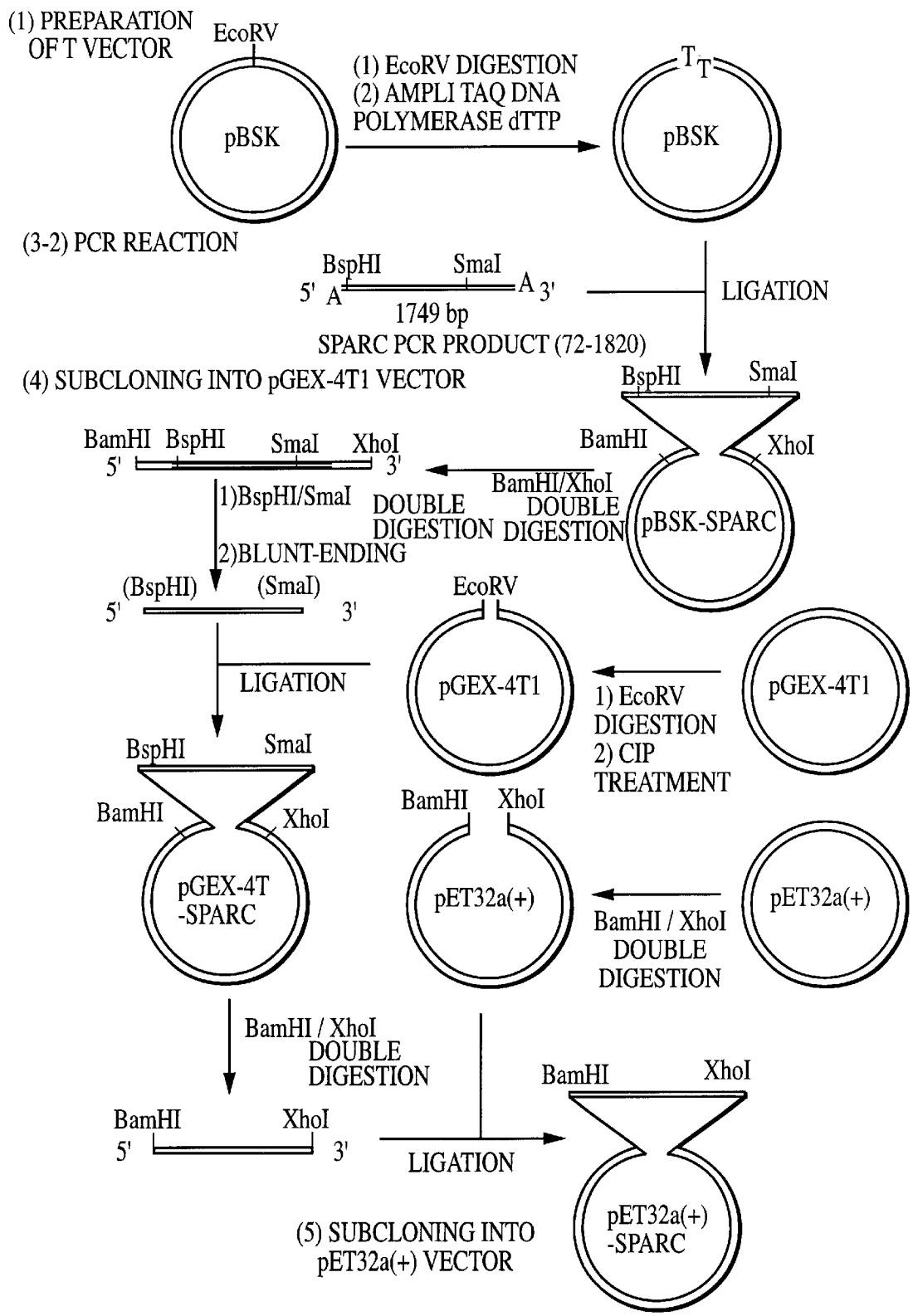
FIG. 2 shows an outline of the construction of pET32a (+)-SPARC vector.

Hereinbelow, the present invention will be described in more detail.

The SPARC fusion protein of the invention is a fusion protein composed of SPARC and thioredoxin. This SPARC fusion protein can be prepared using, for example, a commercial expression vector containing a thioredoxin gene. Briefly, a DNA encoding SPARC (hereinafter referred to as the "SPARC gene") may be inserted into the multi-cloning site of the vector located downstream of the thioredoxin gene, and expressed in a host cell such as *E. coli* in a large quantity.

Hereinbelow, this preparation will be described specifically.

1. Cloning of the SPARC Gene
(1) Amplification of a cDNA Fragment Encoding SPARC
   In the present invention, the cloning of the SPARC gene is performed by RT-PCR. First, total RNA is prepared from tissues or cells expressing SPARC (e.g. mouse cerebral cortex). As a method for preparing total RNA, the acidic guanidine thiocyanate-phenol-chloroform method (AGPC) (P. Chomczynski and N. Sacchi, Analytical Biochemistry, 162: 156, 1987), the guanidine thiocyanate-cesium trifluoroacetate method (H. Okayama et al., Methods in Enzymology, 154: 3, 1987), or the like may be enumerated. The resultant total RNA is subjected to reverse transcription according to the method of, for example, J. Sambrook et al. described in *Molecular Cloning: A Laboratory Manual*, Second Edition, Cold Spring Harbor Laboratory Press, 1989, to thereby convert the mRNA in the total RNA to cDNA. Subsequently, using this cDNA as a template, a PCR is performed using a pair of primers based on the nucleotide sequence of SPARC CDNA which has already been reported (J. H. McVey et al., Journal of Biochemistry, 263: 11111–11116, 1988). Thus, a cDNA fragment encoding SPARC is amplified.

(2) Determination of the Nucleotide Sequence of the Amplified Fragment

The nucleotide sequence of the amplified fragment is determined by cycle sequencing as described below. First, the fragment amplified in (1) above is subcloned into a TA cloning vector such as pbluescript T-vector, pBluescriptII T-vector, pT7Blue T-vector, pT7Blue-2 T-vector. Then, in the presence of a primer such as T7 primer, T3 primer, M13(-20) primer, reverse primer, SK primer, KS primer, R-20mer primer, U-19mer primer, etc., the template DNA is thermally denatured and the above primer is annealed thereto. Then, a sequencing reaction is carried out using fluorescence-labelled ddNTP. These procedures are repeated 30 cycles. The sequencing reaction may be carried out using a thermostable polymerase such as Taq polymerase in a commercial thermal cycler for PCR.

2. Preparation of a Plasmid Vector for Expression of the SPARC Fusion Protein

As a plasmid vector for expressing the SPARC fusion protein, any plasmid vector may be used in the invention as long as it satisfies the following conditions: it is replicable in a host cell to be used; it carries an appropriate transformation marker gene such as ampicillin resistance gene, kanamycin resistance gene, tetracycline resistant gene; when the SPARC gene is ligated downstream of its thioredoxin gene so that these genes come under the control of a promoter operable in the host cell, it can express SPARC in a state of fusion with thioredoxin; and preferably, it is an inducible vector which has low expression levels in the absence of the relevant inducer and has high expression levels when the expression is induced.

It is also desirable that a plasmid vector has an appropriate restriction site for the insertion of a thioredoxin-SPARC cDNA. Specific examples of such a vector include pET vector (Novagen), pTrxFUS vector (Invitrogen) and pCYB vector (New England BioLabs) when the host cell is *E. coli*; pESP-1 expression vector (Stratagene), pAUR123 vector (Takara) and PPIC vector (Invitrogen) when the host cell is yeast; pMAM-neo expression vector (Clontech), pCDNA3.1 vector (Invitrogen) and PBK-CMV vector (Stratagene) when the host cell is an animal cell; pBacPAK vector (Clontech), pAcUW31 vector (Clontech) and pAcP(+)IE1 vector (Novagen) when the host cell is an insect cell.

A promoter useful in the invention is not particularly limited as long as it is operable in individual host cells into which the above vectors are introduced. When *E. coli* is used as the host cell, T7 promoter, T5 promoter, λ $P_L$ promoter, trp promoter, tac promoter, lac promoter or the like may be used. When yeast is used as the host cell, PGK promoter, ADHL promoter, Gall-Gal10 promoter, PH05 promoter or the like may be used. When an animal cell is used as the host cell, SV40 promoter, CMV promoter, CAG promoter, SRα promoter, EF1α promoter, AML promoter, MMTV promoter, MTII promoter or the like may be used. When an insect cell is used as the host cell, P10 promoter, polyhedron promoter or the like may be used.

Alternatively, a commercial expression vector may be used into which a thioredoxin gene has already been inserted so that the gene comes under the control of an appropriate promoter. For example, pET32a(+) vector (Novagen) containing T7 promoter may be used preferably.

A cDNA fragment encoding SPARC is inserted into the above plasmid expression vector at a restriction site located at the C-terminal of its thioredoxin gene so that the reading frame of the cDNA coincides with that of the thioredoxin gene. Thus, a recombinant DNA can be obtained.

Using the resultant recombinant DNA, a host cell is transformed to produce a transformant. As a host cell for producing the SPARC fusion protein, *E. coli, Bactillus subtilis,* yeast, animal cells, insect cells or the like may be used. Preferably, *E. coli* is used. Specific examples of strains useful in the invention include *Escherichia coli* JM109, HB101, BL21, NovaBlue, AD494, B834, HMS174 and BLR. Preferably, a protease-defective strain (such as lon gene-defective strain) of these strains may be used.

Transformation is performed by, for example, the calcium chloride method, electroporation, the rubidium chloride method, lipofection, the DEAE-dextran method, the lithium method, the spheloplast method or methods using virus.

3. Production of the SPARC Fusion Protein

The thus obtained transformant is cultured in a medium so that the SPARC fusion protein is produced and accumulated in the resultant culture. By recovering this protein, the SPARC fusion protein of the invention can be obtained.

The cultivation of the transformant of the invention in a medium may be performed by conventional methods used for culturing the relevant host cell.

As a medium for culturing a transformant obtained from a prokaryote host such as *E. coli* or an eukaryote host such as yeast, either a natural or synthetic medium may be used as long as it contains carbon sources, nitrogen sources and inorganic salts assimilable by the relevant microorganism and is capable of effective cultivation of the transformant.

As carbon sources, any material may be used as long as it is assimilable by the relevant microorganism. Specifically, carbohydrates such as glucose, fructose, sucrose, molasses containing thereof, starch or starch hydrolysate; organic acids such as acetic acid, propionic acid; and alcohols such as ethanol, propanol may be used.

As nitrogen sources, ammonia; ammonium salts of inorganic or organic acids such as ammonium chloride, ammonium sulfate, ammonium acetate, ammonium phosphate; other nitrogen-containing compounds; Peptone; meat extract; yeast extract; corn steep liquor; casein hydrolysate; soybean meal and hydrolysate thereof; cells of various fermenters and digests thereof; etc. may be used.

As inorganic substances, potassium dihydrogen phosphate, dipotassium hydrogen phosphate, magnesium phosphate, magnesium sulfate, sodium chloride, iron(II) sulfate, manganese sulfate, copper sulfate, calcium carbonate and the like may be used.

Specifically, the transformant may be cultured in LB medium, H medium, SOB medium, SOC medium, NZYM medium, TB medium, YT medium, tryptone medium, TYGPN medium, λ medium, super broth medium, M9 medium, M63 medium, A medium or the like.

It is appropriate to adjust the pH of the medium to 6–8. The pH adjustment is carried out using an inorganic or organic acid, an alkali solution, urea, calcium carbonate, ammonia or the like.

Cultivation is carried out at 4–40° C., preferably at 36–38° C., for 1–24 hours, preferable 2–3 hours. If necessary, aeration or agitation may be carried out.

During the cultivation, an antibiotic such as ampicillin or tetracycline may be added to the medium if necessary.

When a microorganism transformed with an expression vector containing an inducible promoter is cultured, an inducer may be added to the medium if necessary. For example, when a microorganism transformed with an expression vector containing lac promoter is cultured, isopropyl-β-D-thiogalactopyranoside or the like may be added to the medium. When a microorganism transformed with an expression vector containing trp promoter is cultured, indoleacrylic acid or the like may be added.

As a medium for culturing a transformant obtained from an animal cell as a host, commonly used RPMI1640 medium, Eagle's MEM medium or DMEM medium, or one of these media supplemented with fetal bovine serum, etc. may be used.

In order to isolate and purify the expressed protein from the culture fluid of the transformant, conventional methods for protein isolation and purification may be used.

The SPARC fusion protein of the invention is expressed in a state of solution in the cytoplasm of the host cell. Therefore, after completion of the cultivation, cells are harvested by centrifugation, suspended in an aqueous buffer and then disrupted with a sonicator, French press, tissue homogenizer, Dynomill or the like to obtain a cell-free extract. This cell-free extract is centrifuged to obtain a supernatant, from which a purified product of the SPARC fusion protein can be obtained by conventional enzyme isolation/purification methods. Specifically, solvent extraction; salting out using ammonium sulfate or the like; desalting; precipitation using an organic solvent; anion exchange chromatography using resins such as diethylaminoethyl (DEAE)Sepharose; cation exchange chromatography using resins such as S-Sepharose FF (Pharmacia); hydrophobic chromatography using a resin such as butyl Sepharose or phenyl Sepharose; gel filtration using molecular sieves; affinity chromatography using resins such as His Bind Resin (Novagen); chromato-focusing; electrophoresis such as isoelectric focusing or the like; is used independently or in an appropriate combination.

It is also possible to cut out SPARC alone from the resultant SPARC fusion protein by using enterokinase or thrombin.

4. Preparation of Pharmaceutical Compositions Comprising the SPARC Fusion Protein Since the SPARC fusion protein of the invention has actions of inhibiting the cell adhesion of nerve cells and causing nerve cell migration, the protein is useful for elucidating mechanisms of all the phenomenons in which nerve cell proliferation, migration and differentiation are involved, e.g. development, aging, metastasis of cancer, healing from injuries, biological defense, etc.

Specifically, the SPARC fusion protein of the invention stimulates such states that occur when nerve cell adhesion is inhibited and nerve cell migration is active, and that are favorable to living organisms. Examples of such states include the process in which injuries are healed, and angiogenesis in the brain (formation of nutrient vessels in arteriosclerotic tunica intima and formation of ventral blood circulation routes at the time of vascular occlusion). Thus, the SPARC fusion protein of the invention may be used as a healing agent for injuries or a prophylactic therapeutic for diseases such as arteriosclerosis, cerebral thrombosis and cerebral embolism. Further, the SPARC fusion protein of the invention may be used as a reagent for searching and studying substances which inhibit such states that progress when nerve cell adhesion is inhibited and nerve cell migration is active, and that are unfavorable to living organisms (e.g. proliferation, metastasis and infiltration of cancer in brain tumor tissues).

The SPARC fusion protein of the invention also has an action of causing neuroplasticity by promoting neurite degeneration. As used herein, the term "neuroplasticity" means to adjust membrane properties characteristic of nerve cells and the strength of synapse linkage between nerve cells by morphologically changing nerve cells. This property (neuroplasticity) makes it possible for living organisms to adapt themselves to changing demands from the environment at every level such as sensory input, association area and motor output.

Therefore, the SPARC fusion protein of the invention is useful afor elucidating mechanisms of all the phenomenons in which the remodeling of synapses is involved, e.g. higher brain functions such as memory, learning; development; nervous dysfunction; etc.

Specifically, the SPARC fusion protein of the invention may be used as a reagent for research to elucidate mechanisms of drug torelance/dependence such as morphine poisoning or as a prophylactic therapeutic for nervous diseases such as epilepsy, dementia, amnesia and psychosis.

The term "anti-cell adhesion activity" used in Test Examples described later means an activity to inhibit the elongation of nerve cells whose shapes have been rounded for some reason, i.e. an activity to maintain nerve cells in a rounded state (wherein these nerve cells in a rounded state are characterized by being alive and adhering). A substance with this activity can contribute in vivo, for example, to a process in which nerve cells damaged by a brain injury are replaced with normal nerve cells.

The term "cell-rounding activity" used herein means an activity to round the shapes of nerve cells which have been elongating and whose neurites have been outgrowing (wherein the resultant rounded nerve cells are characterized as being alive and adhering). A substance with this activity can contribute in vivo, for example, to the phenomenon of neurite degeneration.

Accordingly, the above-described activities of the SPARC fusion protein, which the present inventors confirmed in the test examples, evidence the fact that the protein has activities such as the inhibition of nerve cell adhesion, the resultant induction of nerve cell migration and the remodeling of synapses.

Since the SPARC fusion protein of the invention has various actions as described above, a purified product of this protein obtained in Section 3 above may be formulated by various known methods and provided as pharmaceutical compositions. For example, the purified product may be combined with pharmaceutically acceptable solvents, excipients, carriers, adjuvant, etc. and prepared into injections, powder, granules, tablets, suppositories, entric tablets, capsules, etc. by conventional methods.

The content of the SPARC fusion protein (active ingredient) in the pharmaceutical composition may be about 0.1 to 10% by weight.

When used as a prophylactic therapeutic for the above-described diseases, the pharmaceutical composition may be administered safely to mammals such as human, mouse, rat, rabbit, dog and cat parenterally or orally. The dosage levels of the pharmaceutical composition may be varied appropriately depending on the dosage form, the route of administration, conditions of the subject, and so on. For example, when the pharmaceutical composition is administered to a mammal including human, 1 to 100 mg of the SPARC fusion protein may be administered several times a day.

According to the present invention, SPARC is expected to be utilized as research reagents and pharmaceuticals because of its various physiological activities including angiogenesis, anti-cell adhesion activity, ECM remodeling and bone formation. Moreover, SPARC can be produced as an easy-to-formulate, soluble fusion protein efficiently, economically and in a large quantity without losing its physiological activities.

Further, according to the present invention, a pharmaceutical composition is provided which can be used for studying the mechanism of every change that occurs in nerve cells and synapses (e.g. proliferation, adhesion, migration, excitement); for healing injuries; and for prophylactically treating conditions or diseases attributable to such changes (typically, diseases such as arteriosclerosis which can be improved by angiogenesis in the brain, and nervous diseases such as epilepsy).

Experimental Embodiments of the Invention

Hereinbelow, the present invention will be described in more detail with reference to the following Examples. However, the present invention is not limited to these Examples.

EXAMPLE 1

Preparation of a Plasmid Vector for Expression of the SPARC Fusion Protein (1) Preparation of a T Vector A T vector was prepared according to the method of D. Marchuk et al. (Nucleic Acids Research, 19: 1154, 1990). Briefly, 1.0 $\mu$l of plasmid Bluescript SK(−) (10 $\mu$g/$\mu$l ) (Stratagene), 2.0 $\mu$l of 10×buffer H (Takara), 2.0 $\mu$l of EcORV (10 U/$\mu$l ) and 15.0 $\mu$l of sterilized water were mixed. The total volume was adjusted to 20.0 $\mu$l, and then the mixture was reacted at 37° C. for 2 hours to digest the plasmid completely. Subsequently, the resultant reaction was subjected to ethanol precipitation. To the precipitate, 4.0 $\mu$l of 10×PCR buffer (PE Applied Systems), 8.0 $\mu$l of 10 mM dTTP, 2.0 $\mu$l of Ampli Taq DNA polymerase (5 U/$\mu$l )(PE Applied Systems) and 24.0 $\mu$l of sterilized water were added. The total volume was adjusted to 40.0 $\mu$l and then the mixture was reacted at 70° C. for 2 hours. After phenol/chloroform extraction and ethanol precipitation for purification and concentration, the resultant precipitate was dissolved in 20 $\mu$l of sterilized water to obtain a solution of T vector, which was stored at 4° C. or below.

(2) Extraction of Total RNA from Mouse Cerebral Cortex

Total RNA was extracted according to the method of P. Chomczynski et al. (Analytical Biochemistry, 162: 156–159, 1987). Briefly, mouse cerebral cortex was removed, frozen in liquid nitrogen and disrupted into powder using a hammer. Then, 75 mg of this powder was dissolved in 500 $\mu$l of guanidine solution (4 M guanidine thiocyanate, 25 mM sodium citrate, pH 7.0, 0.5% sodium sarcosyl, 0.1 M mercaptoethanol). To the resultant solution, 50 $\mu$l of 2 M sodium acetate (pH 4.0), 50 $\mu$l of DEPC-treated water-saturated phenol (pH 4.0) and 100 $\mu$l of chloroform were added and agitated. The resultant mixture was left at 4° C. for 15 minutes. After centrifugation at 10,000 g for 20 minutes, the aqueous layer was recovered. An equal volume (600 $\mu$l ) of cooled isopropanol and 2 $\mu$l of glycogen (20 $\mu$g/$\mu$l) were added to the layer, which was then left at −20° C. for 1 hour. After centrifugation at 16,000 g for 10 minutes, the resultant precipitate was dissolved completely in 500 $\mu$l of guanidine solution, and the above-described procedures were repeated again. To the precipitate generated by isopropanol precipitation, 50 $\mu$l of DEPC-treated water was added to thereby obtain a solution of total RNA. Finally, 254 $\mu$g of total RNA was obtained from 0.3 g of mouse cerebral cortex.

(3) Cloning of Mouse SPARC Gene by RT-PCR (3-1) Synthesis of Single-Stranded cDNA To 1.2 $\mu$l of the total RNA (2.5 $\mu$g/$\mu$l) obtained in (2) above, 1.0 $\mu$l of random primers (100 ng/$\mu$l ) and 2.8 $\mu$l of DEPC-treated sterilized water were added. After adjusting the total volume to 5.0 $\mu$l the solution was thermally denatured at 70° C. for 10 minutes. To the resultant solution, 2.0 $\mu$l of 5×buffer (GIBCO BRL), 2.0 $\mu$l of 0.1 M dithiothreitol, 8.0 $\mu$l of 1.25 mM dNTP and 1.0 $\mu$l of Superscript™ II Reverse Transcriptase (200 U/$\mu$l ) were added. After adjusting the total volume to 20.0 $\mu$l the solution was reacted at 42° C. for 2 hours. Further, the reaction solution was thermally treated at 70° C. for 15 minutes to thereby completely deactivate the reverse transcriptase. Thus, a solution of single-stranded cDNA was obtained.

(3-2) PCR Reaction

To 5.0 $\mu$l of the single-stranded cDNA solution obtained in (3-1) above, 2.5 $\mu$l of 10×PCR buffer (PE Applied Systems), 0.25 $\mu$l of Ampli Taq DNA polymerase (5 U/$\mu$l) (PE Applied Systems), 8.0 $\mu$l of 1.25 mM dNTP, 2.5 $\mu$l each of primer 1 (5'-CCGAGAGTTCCCAGCATCAT-3'; 20mer; SEQ ID NO:3 of the Sequence Listing) (60 ng/$\mu$l ) and primer 2 (5'-TCAAACCAATTCACCAGTCT-3'; 20mer; SEQ ID NO:4 of the Sequence Listing) (60 ng/$\mu$l ) and 4.25 $\mu$l of sterilized water were added. The total volume was adjusted to 25.0 $\mu$l to prepare a reaction solution. Then, using DNA Thermal Cycler PJ2000 Model 480 (PE Applied Systems), PCR was performed 35 cycles (denaturation: at 94° C. for 30 seconds; annealing: at 50° C. for 45 seconds; synthesis: at 72° C. for 90 seconds), followed by final extension at 72° C. for 10 minutes. A PCR product of approximately 1750 bp was separated and purified by 1% agarose gel electrophoresis and recovered from the gel with Ultrafree MC Filter (Millipore). The recovered PCR product was subcloned into the above-described T vector using DNA Ligation Kit Ver. 2 (Takara). The PCR primers described above were prepared by chemically synthesizing oligonucleotide sequences which correspond to parts of the mouse SPARC cDNA sequence (J. H. McVey et al., Journal of Biochemistry 263, 11111–11116, 1988). More specifically, primer 1 corresponds to from position 72 to position 91 of the mouse SPARC cDNA sequence, and primer 2 from position 1801 to position 1820 thereof.

(3-3) Determination of the cDNA Sequence of the PCR Product

The cDNA sequence of the T vector into which the above PCR product had been subcloned (pBSK-SPARC vector) was determined by cycle sequencing. Briefly, the T vector was purified with QIAGEN Plasmid Mini kit (Funakoshi). Using 1.5 $\mu$g of this purified vector as a template, a sequence sample was prepared with PRISM Ready Reaction Terminator Cycle Sequencing Kit (PE Applied Systems). The PCR reaction was performed using DNA Thermal Cycler PJ2000 Model 480 (PE Applied Systems) under the following conditions: denaturation: at 96° C. for 30 seconds; annealing: at 50° C. for 15 seconds; synthesis: at 60° C. for 240 seconds; 25 cycles. After removal of unreacted materials by ethanol precipitation, the PCR product was dissolved in 4.0 µl of denaturing solution (5 mg/ml blue dextran, 8.3 mM EDTA, pH 8.0, 83.3% formamide) and denatured at 90° C. for 2 minutes. Immediately thereafter, the cDNA sequence of the PCR product was analyzed with ABI 373S sequencer (PE Applied Systems). As a result, it was confirm that the PCR product contained the mouse SPARC cDNA sequence (72–1820).

(4) Subcloning into PGEX 4T-1 Vector

To 10 µl of PBSK-SPARC vector (6.25 µg/µl) prepared in (3) above, 10 µl of 10×buffer 4 (NEB), 2 µl of BamHI (12 U/µl), 2 µl of XhoI (12 U/µl) and 76 µl of sterilized water were added to make the total volume 100 µl. This solution was reacted at 37° C. for 2 hours. A BamHI-XhoI fragment of approximately 1800 bp was separated and purified by 1% agarose gel electrophoresis, recovered from the gel using Gene Clean II kit (Funakoshi) and dissolved in 48 µl of TE solution (Tris-HCl, pH 8.0, 0.5 mM EDTA, pH 8.0). Then, to 42 µl of this BamHI-XhoI fragment solution, 10 µl of 10×buffer 4 (NEB), 2 µl of BspHI (10 U/µl), 2 µl of SmaI (10 U/µl) and 44 µl of sterilized water were added to make the total volume 100 µl. This solution was reacted at 37° C. for 2 hours. A BspHI-SmaI fragment of approximately 1500 bp was separated and purified by 1% agarose gel electrophoresis, recovered from the gel using Gene Clean II kit (Funakoshi) and dissolved in 48 µl of TE solution. This BspHI-SmaI fragment (960 ng) was blunt-ended using DNA Blunting Kit (Takara) and dissolved in 10 µl of TE solution to obtain a solution of the blunt-ended BspHI-SmaI fragment.

On the other hand, to 2 µl of pGEX-4T1 vector (500 ng/µl) (Pharmacia Biotech), 2 µl of 10×buffer 4 (NEB), 1 µl of SmaI (10 U/µl) and 15 µl of sterilized water were added. After adjusting the total volume to 20 µl the solution was reacted at 37° C. for 2 hours. The reaction solution was subjected to phenol chloroform extraction and ethanol precipitation for purification and concentration. To the resultant precipitate, 5 µl of 10×dephosphorylation buffer (Takara), 1 µl of calf intestine alkaline phosphatase (CIP) (10 U/µl) and 44 µl of sterilized water to make the total volume 50 µl. This solution was reacted at 37° C. for 15 minutes for dephosphorylation. After a thermal treatment at 52° C. for 15 minutes to deactivate the phosphatase, the reaction solution was subjected to phenol chloroform extraction and ethanol precipitation for purification and concentration. The precipitate generated was dissolved in 20 µl of TE solution to thereby obtain a solution of dephosphorylated pGEX-4T1 vector.

Finally, 20 µl of this solution of dephosphorylated pGEX-4T1 vector was mixed with 10 µl of the solution of the blunt-ended BspHI-SmaI fragment and concentrated by ethanol precipitation, followed by ligation of the blunt-ended BspHI-SmaI fragment to the SmaI site of pGEX-4T1 vector using DNA Ligation Kit Ver. 2 (Takara). Thus, pGEX-4T-SPARC vector was obtained. The confirmation that the blunt-ended BspHI-SmaI fragment was incorporated into pGEX-4T1 vector in an expected manner was made by subcloning the BamHI-XhoI fragment of pGEX-4T-SPARC vector into the BamHI-XhoI site of pbluescript SK(−) vector (Stratagene) and analysing the cDNA sequence of this fragment.

(5) Preparation of pET32a(+)-SPARC Vector

To 40 µl of pGEX-4T-SPARC vector (0.25 g g/µl) prepared in (4) above, 10 µl of 10×buffer K (Takara), 2 µl of BamHI (10 U/g l), 2 µl of XhoI (12 U/µl) and 46 µl of sterilized water were added to make the total volume 100 µl. This solution was reacted at 37° C. for 2 hours. The BamHI-XhoI fragment was separated and purified by 1% agarose gel electrophoresis, recovered from the gel using Gene Clean II kit (Funakoshi) and dissolved in 48 µl of TE solution. Subsequently, this fragment was subcloned into the BamHI-XhoI site of pET32a(+) vector (Novagen). The cDNA sequence of the finally obtained pET32a(+)-SPARC vector was analyzed to thereby confirm that the reading frame of the inserted BamHI-XhoI fragment coincides with that of pET32a(+) vector. The entire cDNA sequence of pET32a(+)-SPARC vector is shown in SEQ ID NO:2. The entire amino acid sequence of the SPARC fusion protein expressed by this vector is shown in SEQ ID NO:1 and FIG. 1. And, an outline of the construction of pET32a(+)-SPARC vector explained above is shown in FIG. 2.

EXAMPLE 2

Production of the SPARC Fusion Protein

Figure 3:
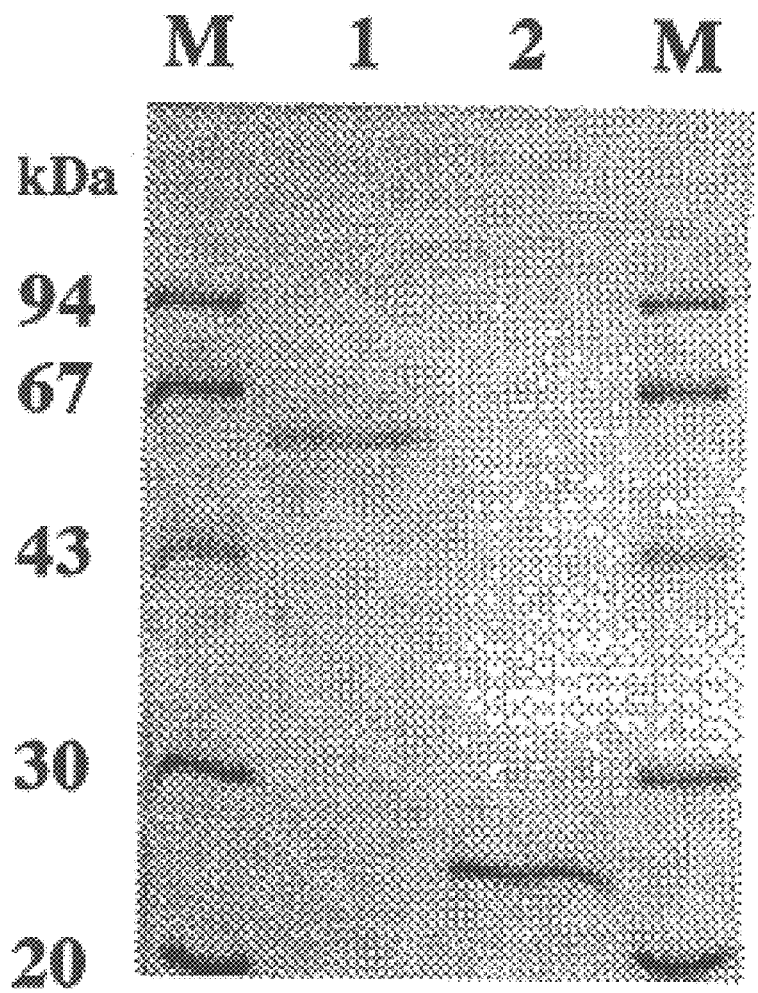
FIG. 3 shows the results of gel electrophoresis (SDS-PAGE) of a purified product of the SPARC fusion protein.

E. coli AD494 (DE3) was transformed with pET32a(+)-SPARC vector prepared in Example 1. The resultant cells were cultured at 37° C. for 3 hours in LB solution containing 30 µg/ml kanamycin until $OD_{560}$ reached 0.6, and then cultured in the presence of 1 mM IPTG at 20° C. for 6 hours under shaking. Thereafter, the cells were harvested by centrifugation (at 6,000×g for 30 minutes), suspended in 20 ml of buffer A (5 mM imidazole, 500 mM NaCl, 20 mM Tris-HCl, pH 7.9) and sonicated. Soluble fractions were recovered by centrifugation at 30,000×g for 30 minutes. These fractions were applied to His Bind Resin Column (Novagen), followed by elution of the adsorbate with buffer B (1 M imidazole, 500 mM NaCl, 20 mM Tris-HCl, pH 7.9). The eluate was concentrated to approximately 1 ml, dialyzed overnight against buffer C (10 mM Tris-HCl, pH 7.4, 100 mM NaCl, 0.1% NP-40) and then applied to a gel filtration column (Superdex 75; Pharmacia). Buffer D (10 MM Tris-HCl, pH 7.4, 100 mM NaCl) was fed to the column at a flow rate of 1 ml/min. Fractionation was carried out by 5 ml. A single peak at retention time 40 min. (fractions 8–10) was recovered and dialyzed against buffer B overnight. This sample was separated by 10% SDS-pAGE and then stained with CBB. As a result, it was confirmed that the thus purified sample is a single band of 25 kDa and has a purity of 98% or more (FIG. 3). The yield was approximately 1 mg per liter of LB culture liquid.

EXAMPLE 3

Identification of Drug Tolerance/Dependence-Related Genes and Analysis Thereof

A morphine tolerance/dependence model mouse was created by administering morphine hydrochloride to ddy mice (male; 6-week old) subcutaneously at doses of 10 mg/kg (day 1), 20 mg/kg (day 2), 40 mg/kg (day 3), 80 mg/kg (day 4), 100 mg/kg (day 5), 100 mg/kg (day 6) and 100 mg/kg (day 7) two times a day for 7 days. From these mice which received chronic administration of morphine and control mice which received administration of physiological saline alone, the amygdala was removed. Poly(A) RNA (5 µg) was prepared therefrom and λ ZapII cDNA library was constructed using Zap-cDNA synthesis kit (Stratagene). Subsequently, a substracted cDNA library was constructed by substracting mRNA by the photobiotin-avidin method, followed by differential hybridization to thereby isolate a group of candidate genes related to drug tolerance/ dependence. Results of in situ hybridization revealed that mRNA expression in the amygdala is specifically increased during chronic administration of morphine, and that a gene which is antagonized by naloxone exists in the candidate genes. As a result of cDNA analysis, it was found that this gene is the SPARC gene.

Then, using the above-mentioned ddy mice (male; 6-week old), changes in SPARC mRNA expression as a result of morphine administration were analyzed in detail. Morphine administration was performed by the following 3 ways:

(1) chronic administration: morphine hydrochloride was administered subcutaneously at doses of 10 mg/kg (day 1), 20 mg/kg (day 2), 40 mg/kg (day 3), 80 mg/kg (day 4), 100 mg/kg (day 5), 100 mg/kg (day 6) and 100 mg/kg (day 7) two times a day for 7 days;

(2) acute administration: morphine hydrochloride was administered once subcutaneously at a dose of 100 mg/kg;

(3) joint administration: an equal amount of naloxone was administered jointly at each time morphine hydrochloride was administered in the chronic administration described in (1).

Figure 4A:
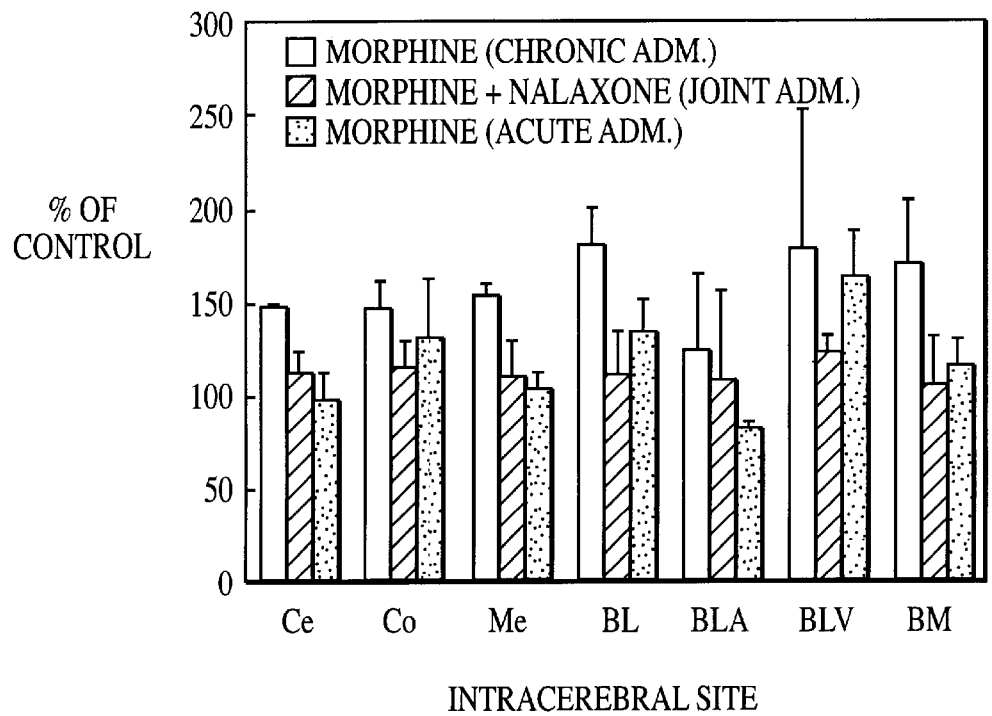
FIG. 4, panel A shows changes in the expression of SPARC mRNA in various sites of the amygdala (Ce: central amygdala nucleus; Co: cortical amygdala nucleus; Me: medial amygdala nucleus; BL: basolateral amygdala nucleus; BLA: basolateral amygdala nucleus, anterior part; BLV: basolateral amygdala nucleus, ventral part; BM: basomedial amygdala nucleus) and the locus ceruleus (LC) as a result of morphine administration, compared to the corresponding expression in control.
Figure 4B:
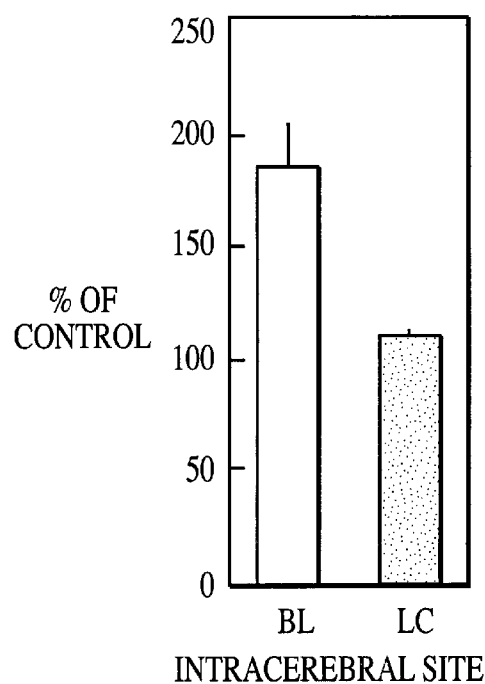

Panel A in FIG. 4 shows amount ratios of SPARC mRNA expression at various sites of the amygdala (Ce: central amygdala nucleus; Co: cortical amygdala nucleus; Me: medial amygdala nucleus; BL: basolateral amygdala nucleus; BLA: basolateral amygdala nucleus, anterior part; BLV: basolateral amygdala nucleus, ventral part; BM: basomedial amygdala nucleus) in administration group mice to that expression at corresponding sites in control mice (physiological saline alone). Panel B in FIG. 4 shows amount ratios of SPARC mRNA expression at the basolateral amygdala nucleus (BL) of the amygdala and at the locus ceruleus (LC) outside of the amygdala in administration group mice to that expression at corresponding sites in control mice (physiological saline alone). SPARC mRNA expression is high at any of the sites tested in the amygdala in the chronic administration group (FIG. 4a). However, no increase in SPARC mRNA expression was recognized at the locus ceruleus (LC) involved in dependence symptoms, regardless of the administration method (FIG. 4b).

Figure 5:
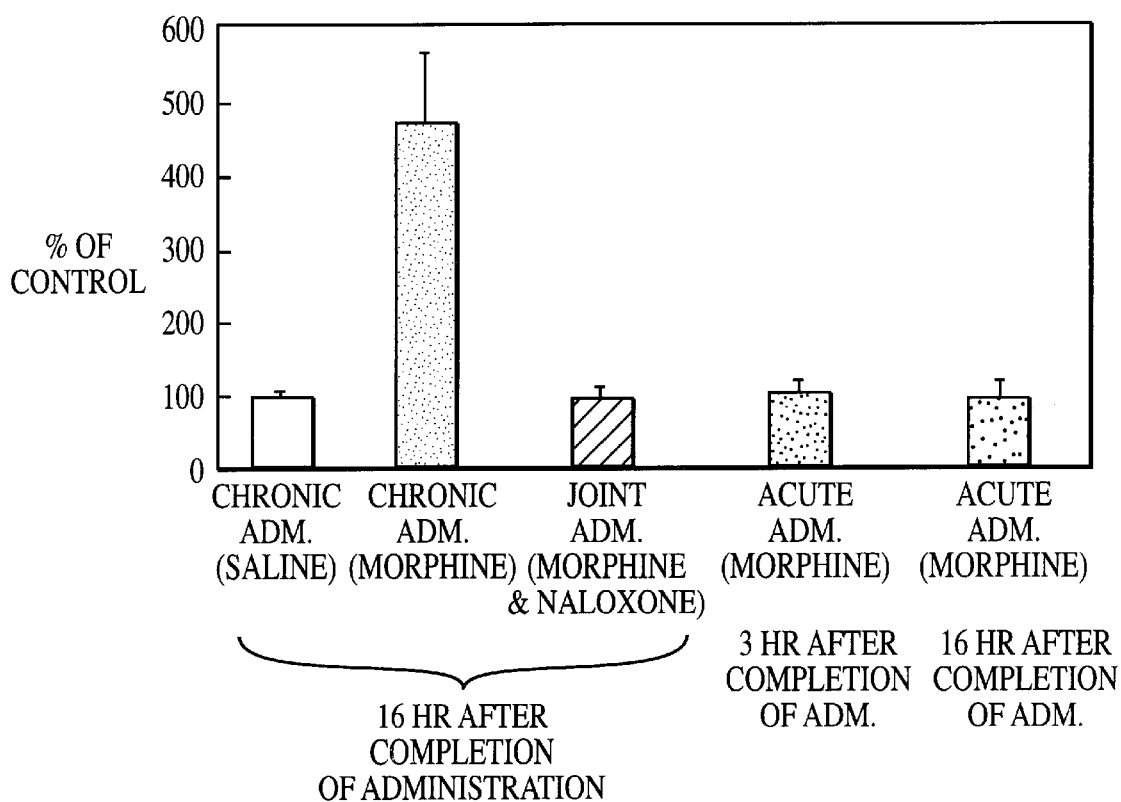
FIG. 5 shows changes in the expression of SPARC mRNA in the basolateral amygdala nucleus (BL) of the amygdala as a result of morphine administration by various methods (chronic, acute and joint administration), compared to the corresponding expression in control.

SPARC MRNA expression at the basolateral amygdala nucleus (BL) of the amygdala was examined further. As a result, a remarkable, 4- to 5-fold increase was recognized in the chronic administration group alone (FIG. 5).

The amount of SPARC mRNA expression was determined 16 hours after the completion of administration in the chronic and joint administration, while it was determined 3 hours after the administration (FIG. 4) or 3 hours and 16 hours after the administration (FIG. 5) in the acute administration.

Figure 6:
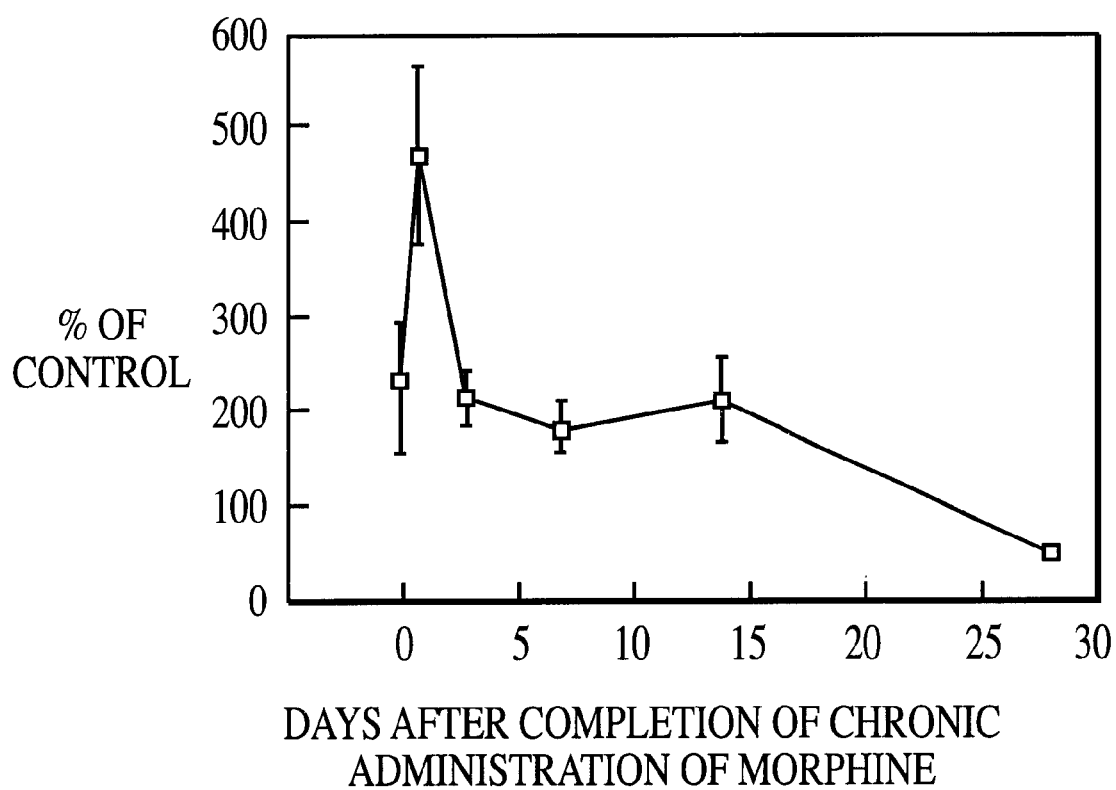
FIG. 6 shows the time course of SPARC mRNA in the basolateral amygdala nucleus (BL) of the amygdala after the termination of morphine administration.

Increase in SPARC mRNA was confirmed in the basolateral amygdala nucleus (BL) for at least 2 weeks after the termination of morphine administration (FIG. 6).

EXAMPLE 4

Analysis of the Intracerebral Function of the SPARC Fusion Protein

Morphine or physiological saline was administered to mice chronically under the same conditions as in Example 3. One, two and four weeks after the completion of the chronic administration, morphine (100 mg/kg) was subcutaneously administered once, followed by determination of morphine-induced spontaneous locomotor activity. One and two weeks after the completion of the administration, a remarkable enhancement in spontaneous locomotor activity was observed in the morphine chronic administration group compared to the physiological saline administration group. However, no enhancement effect was recognized four weeks after the completion of the administration. These results strongly correlate with the time course of the SPARC mRNA expression increase in the basolateral amygdala nucleus (BL) of the amygdala after completion of the chronic administration of morphine.

Figure 7:
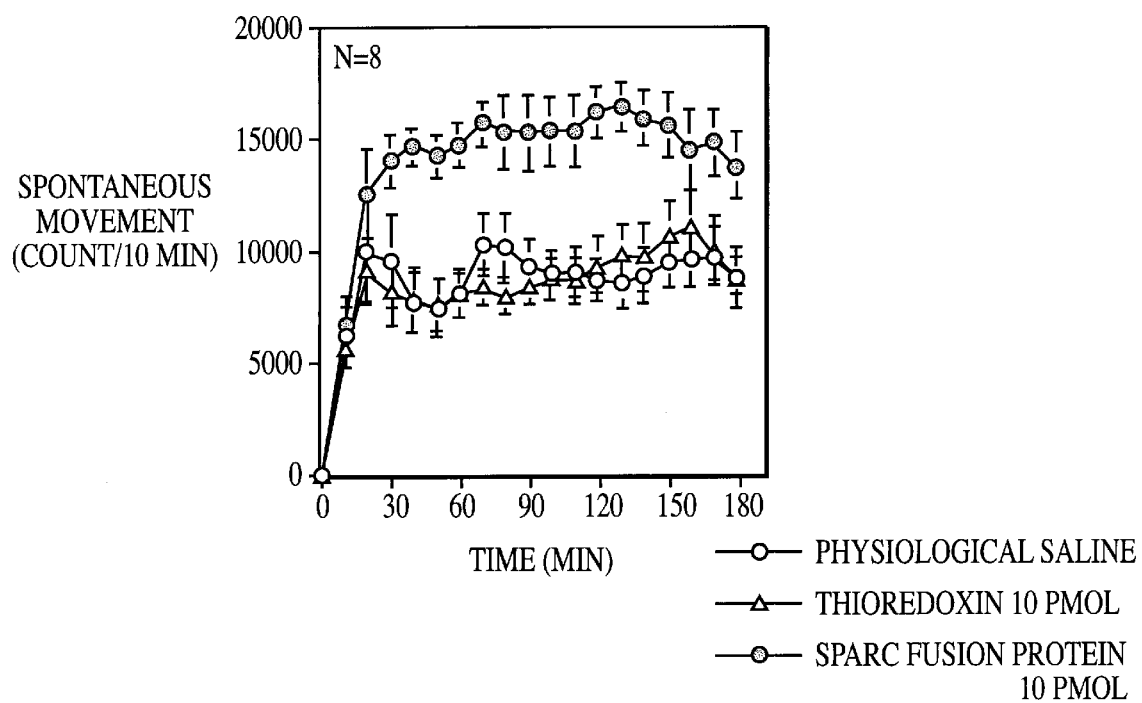
FIG. 7 shows the enhancement of morphine-induced spontaneous locomotor activity as a result of intracerebral administration of the SPARC fusion protein.

Then, 10 pmol SPARC fusion protein prepared in Example 2 was injected into the lateral basal ganglia (BL) at both sides of mouse amygdala (B: 1.6 mm; L: 3.0 mm; V: 3.0 mm) in an amount of 0.5 μl, followed by subcutaneous administration of morphine (100 mg/kg) 2 days thereafter. As a result, a remarkable enhancement in spontaneous movement was recognized in test mice, compared to control mice to which thioredoxin or physiological saline was injected instead of the SPARC fusion protein in the same manner as described above (FIG. 7). Thus, it was confirmed that the SPARC fusion protein causes enhancement in morphine-induced spontaneous locomotor activity in the brain.

EXAMPLE 5

Anti-Cell Adhesion Effect and Cell-Rounding Effect on Nerve Cells

Using representative cultured nerve cells C6Bu-1 (rat glioma cells), N18TG-2 (mouse neuroblastoma cells) and NG108-15 (hybrid between C6BU-1 and N18TG-2), the anti-cell adhesion activity and cell-rounding activity of the SPARC fusion protein were examined as described below. Hereinbelow, the term "cultured nerve cells" means the above cytomas.

(1) Anti-Cell Adhesion Activity

The cultured nerve cells were proliferated in Dulbecco's Modification of Eagle's Minimal Essential Medium containing 10% fetal calf serum (10% FCS-DMEM solution) in a $CO_2$ incubator at 37° C. under 5% $CO_2$ until cells reached subconfluence. The resultant cells were washed with PBS(−) solution twice, completely stripped off from the culture dish with a solution containing PBS(−) and 0.5 mM EDTA, and then suspended in 5% FCS/DMEM solution to give a density of $1 \times 10^6$ cells/ml, to thereby obtain a cell suspension. On the other hand, 70 μl of 5% FCS-DMEM solution and 10 μl of SPARC fusion protein solution in PBS(−) adjusted to a desired concentration were dispensed to each well of a 96-well plate (Falcon) and agitated lightly. This plate was kept in a $CO_2$ incubator at 37° C. under 5% $CO_2$ for 15 minutes. Then, 20 μl of the above-described cell suspension was added to each well and agitated lightly again. This plate was incubated in a $CO_2$ incubator at 37° C. under 5% $CO_2$ for 48 hours. After the incubation, each well was microscopically examined and photographed. The ratio of rounded cells was calculated by determining the number of cells which were rounded and the number of cells which were not rounded.

(2) Cell-Rounding Activity

A cell suspension (100 μl) prepared in the same manner as in (1) above was dispensed to each well of a 96-well plate (Falcon) and cultured in a $CO_2$ incubator at 37° C. under 5% $CO_2$ for 48 hours. After confirming that cultured nerve cells were adhering and elongating, the cells were washed gently with PBS(−) solution. Then, 90 μl of 5% FCS-DMEM solution and 10 μl of SPARC fusion protein solution in PBS(−) adjusted to a desired concentration were added to each well and agitated lightly. This plate was incubated in a $CO_2$ incubator under 5% $CO_2$ at 370° C. for 24 hours. Then, each well was microscopically examined and photographed. The ratio of rounded cells was calculated by determining the number of cells which were rounded and the number of cells which were not rounded.

Figure 8A:
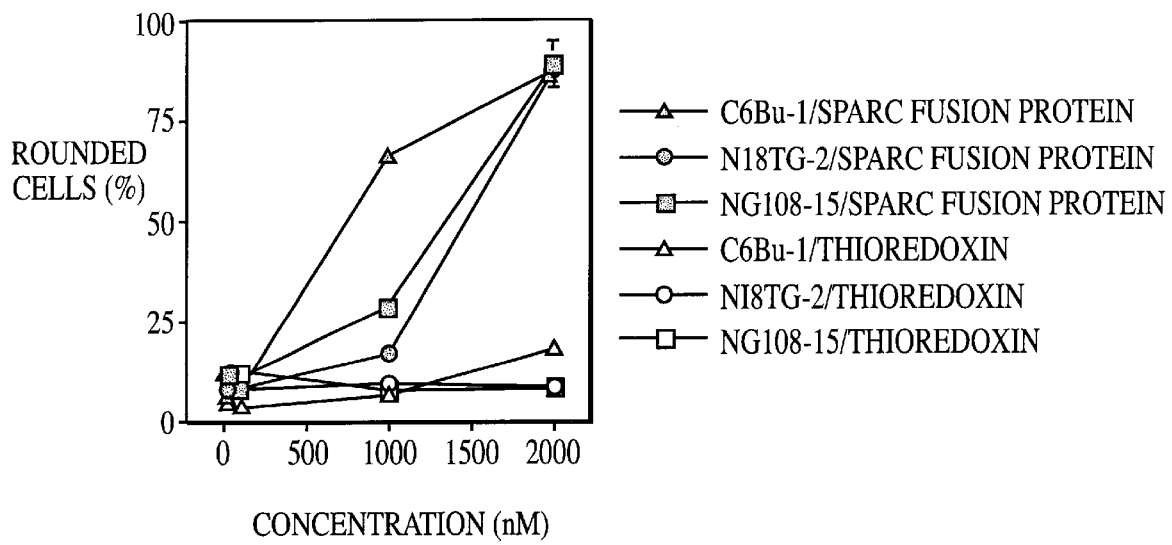
FIG. 8, Panel A shows the anti-cell adhesion activity of the SPARC fusion protein as a function of concentration, while FIG. 8, Panel B shows the anti-cell adhesion activity of the SPARC fusion protein corresponding with the treatment method.
Figure 8B:
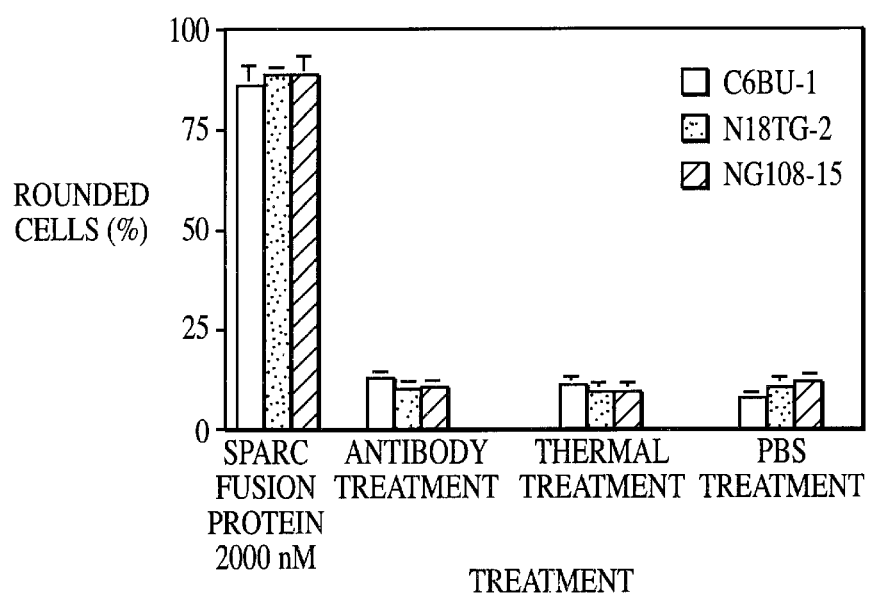
Figure 9A:
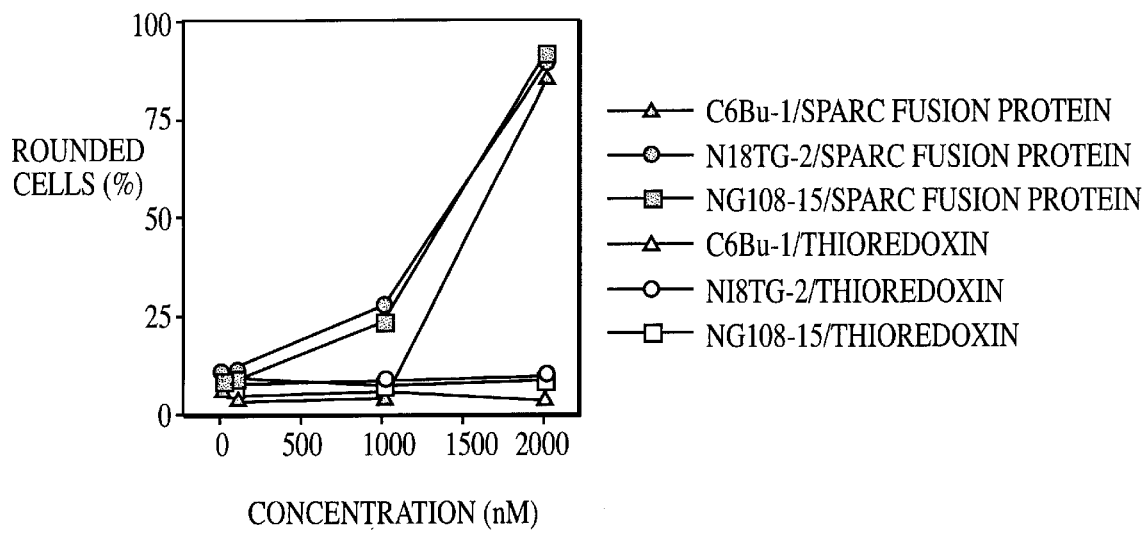
FIG. 9 Panel A shows the cell-rounding activity of the SPARC fusion protein as a function of concentration, while FIG. 8, Panel B shows the cell-rounding activity of the SPARC fusion protein corresponding with the treatment method.
Figure 9B:
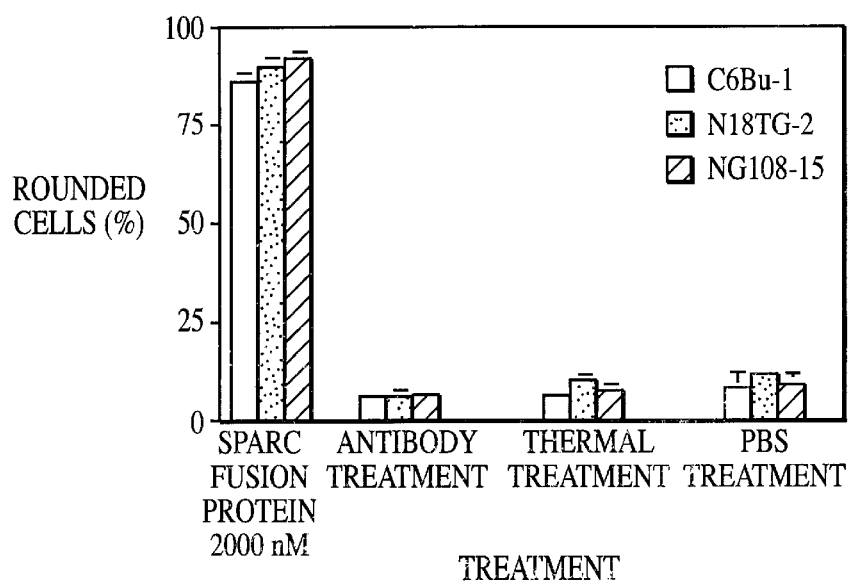

As a result, both anti-cell adhesion effect and cell-rounding effect of the SPARC fusion protein were recognized in a concentration dependent manner (FIG. 8a, FIG. 9a). These effect were completely eliminated by pre-treatment of the protein with a polyclonal antibody, thermal treatment of the protein (at 90° C. for 15 minutes) or PBS treatment of the protein. It was also confirmed that sensitivity to both effects is different between glioma cells and neuroblastoma cells.

What is claimed is:

1. The isolated fusion protein as set forth in SEQ ID NO:2, wherein said fusion protein inhibits nerve cell adhesion to plastic.

2. A composition comprising the fusion protein of claim 1.

3. An isolated nucleic acid encoding the fusion protein of claim 1.

4. The nucleic acid of claim 3, wherein said nucleic acid comprises deoxyribonucleic acid.

5. An isolated nucleic acid comprising nucleotide 5209 through nucleotide 6609 of SEQ ID NO:1.

6. A recombinant vector encoding the fusion protein of claim 1.

7. A method for producing a secreted protein acidic and rich in cysteine, comprising the steps of:
 a) providing:
  i) a host cell, and
  ii) the vector of claim 6; and
 b) introducing said vector into said host cell under conditions such that a secreted protein acidic and rich in cysteine is produced.

8. The method of claim 7, further comprising the step of recovering said secreted protein acidic and rich in cysteine.

9. The secreted protein acidic and rich in cysteine produced according to the method of claim 7.

* * * * *